US010614917B2

(12) United States Patent
Gemmel et al.

(10) Patent No.: US 10,614,917 B2
(45) Date of Patent: Apr. 7, 2020

(54) MEDICAL APPARATUS AND METHOD OF CONTROLLING A MEDICAL APPARATUS

(71) Applicant: SIEMENS HEALTHCARE GMBH, Erlangen (DE)

(72) Inventors: Alexander Gemmel, Erlangen (DE); Hans Schweizer, Plattling (DE); Wei Wei, Forchheim (DE); Markus Weiten, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 392 days.

(21) Appl. No.: 15/241,303

(22) Filed: Aug. 19, 2016

(65) Prior Publication Data

US 2017/0052670 A1 Feb. 23, 2017

(30) Foreign Application Priority Data

Aug. 19, 2015 (DE) .................... 10 2015 215 820

(51) Int. Cl.
*G16H 40/63* (2018.01)
(52) U.S. Cl.
CPC .................. *G16H 40/63* (2018.01)
(58) Field of Classification Search
CPC .................. G06F 3/04842; G06F 19/00
See application file for complete search history.

(56) References Cited

U.S. PATENT DOCUMENTS

| 8,255,060 | B2 * | 8/2012 | Goetz | A61N 1/37247 |
| | | | | 607/59 |
| 2003/0008709 | A1 * | 1/2003 | Higashida | G05D 1/0033 |
| | | | | 463/39 |
| 2003/0195644 | A1 * | 10/2003 | Borders | A47C 31/008 |
| | | | | 700/90 |
| 2005/0065435 | A1 * | 3/2005 | Rauch | A61B 34/73 |
| | | | | 600/427 |
| 2006/0025679 | A1 * | 2/2006 | Viswanathan | A61B 6/548 |
| | | | | 600/424 |
| 2007/0086570 | A1 * | 4/2007 | Spahn | A61B 6/102 |
| | | | | 378/117 |
| 2008/0009958 | A1 * | 1/2008 | Abt | B60N 2/0244 |
| | | | | 700/29 |
| 2008/0235872 | A1 * | 10/2008 | Newkirk | A61G 7/018 |
| | | | | 5/600 |
| 2009/0112630 | A1 * | 4/2009 | Collins, Jr. | G16H 40/20 |
| | | | | 705/3 |
| 2009/0119609 | A1 * | 5/2009 | Matsumoto | G06F 3/04817 |
| | | | | 715/769 |
| 2009/0281452 | A1 * | 11/2009 | Pfister | A61B 6/12 |
| | | | | 600/567 |

(Continued)

*Primary Examiner* — Ryan F Pitaro
(74) *Attorney, Agent, or Firm* — Laurence Greenberg; Werner Stemer; Ralph Locher

(57) ABSTRACT

A medical apparatus has a plurality of movable elements that are remotely displaced. A display device receives inputs for positioning the movable elements from a user. A computing device that is coupled to the display device displays a model of the medical apparatus on the display device. The movable elements are displayed in the model in accordance with the received inputs for positioning. In response to a trigger signal of the user for moving the movable elements, the movable elements are driven so as to adopt the displayed position.

14 Claims, 5 Drawing Sheets

(56) References Cited

U.S. PATENT DOCUMENTS

| | | | |
|---|---|---|---|
| 2010/0017033 A1* | 1/2010 | Boca | B25J 9/0093 700/258 |
| 2010/0017730 A1* | 1/2010 | Coppedge, III | G06F 17/24 715/764 |
| 2010/0081914 A1 | 4/2010 | Waynik et al. | |
| 2012/0136480 A1* | 5/2012 | Lee | A61B 6/4441 700/255 |
| 2012/0174022 A1* | 7/2012 | Sandhu | G06F 19/3406 715/781 |
| 2013/0165854 A1 | 6/2013 | Sandhu et al. | |
| 2013/0293173 A1* | 11/2013 | Strothmann | A47B 9/20 318/466 |
| 2014/0149910 A1* | 5/2014 | Lee | A61B 6/465 715/771 |
| 2014/0304638 A1* | 10/2014 | Yoshikawa | A61B 6/465 715/771 |
| 2015/0134145 A1* | 5/2015 | Lee | A61B 19/5244 701/2 |
| 2015/0317068 A1* | 11/2015 | Marka | A61G 13/02 715/835 |
| 2015/0379221 A1* | 12/2015 | Yeager | G16H 40/40 715/771 |
| 2016/0274782 A1* | 9/2016 | Keil | A61B 5/7435 |
| 2017/0065239 A1* | 3/2017 | Higuma | A61B 6/032 |
| 2017/0251992 A1* | 9/2017 | Jang | A61B 6/541 |
| 2018/0055469 A1* | 3/2018 | Nam | A61B 6/485 |

\* cited by examiner

MEDICAL APPARATUS AND METHOD OF CONTROLLING A MEDICAL APPARATUS

CROSS-REFERENCE TO RELATED APPLICATION

This application claims the priority, under 35 U.S.C. § 119, of German patent application DE 10 2015 215 820.9, filed Aug. 19, 2015; the prior application is herewith incorporated by reference in its entirety.

BACKGROUND OF THE INVENTION

Field of the Invention

The invention relates to a medical technological apparatus, medical apparatus for short, and to a corresponding method for controlling a medical technological apparatus.

Modern medicine uses a multiplicity of medical technological apparatuses or examination apparatuses which enable recordings from the interior of a human body, for example, with the aid of imaging methods.

One example of such apparatuses is C-arm apparatuses or C-arms, which are very large and can be placed, for example, in the form of an arc around the body of a patient. In order to be able to move the individual elements of such a C-arm, electric motors that move the individual elements are used in part nowadays.

Joysticks or buttons arranged on an operating console are typically used for driving the electric motors. In this case, the relation of a joystick or button to the corresponding movement axis of the medical technological apparatus is often not obvious and the driving of the medical technological apparatus is therefore not very intuitive and is susceptible to errors. In particular, the movement direction triggered by an operating element, e.g. a button with an arrow pointing toward the left, may change depending on the location of the operating console and orientation of the medical technological apparatus.

Published patent application US 2013/0165854 A1 describes a control system for a medical catheter guide system. Published patent application US 2010/0081914 A1 describes a system for positioning a guide in a human body.

SUMMARY OF THE INVENTION

It is accordingly an object of the invention to provide a method of controlling the drive of a medical apparatus which overcomes the above-mentioned and other disadvantages of the heretofore-known devices and methods of this general type and which provides for the improved driving of medical technological apparatuses.

With the foregoing and other objects in view there is provided, in accordance with the invention, a medical technological apparatus (medical apparatus, for short), comprising:
a plurality of movable elements;
a display device and an input device being a touch-sensitive screen configured to receive inputs for positioning said movable elements from a user;
a computing device connected to said display device and configured to receive input commands for positioning said movable elements via said input device, said computing device being configured to display a model of the medical apparatus on said display device, to display said movable elements in the model in accordance with the input commands received from said input device and, in response to a trigger signal input by a user, to drive said movable elements to adopt a position as displayed on said display device; and
said computing device being configured to identify in a representation of the model on the touch-sensitive screen those features of the medical apparatus which serve for moving said movable elements and said input device being configured to accept inputs for positioning one of said movable elements only at a correspondingly identified location in the model.

With the above and other objects in view there is also provided, in accordance with the invention, a method of controlling a medical apparatus. The novel method comprises:
displaying a model of the medical apparatus on a touch-sensitive screen, and thereby identifying those features of the medical apparatus in the representation of the model on the touch-sensitive screen which serve for moving movable elements on the medical apparatus;
receiving inputs for positioning the movable elements entered by a user via the touch-sensitive screen, and thereby only accepting inputs for positioning one of the movable elements only at a correspondingly identified location in the model;
displaying the movable elements in the model in accordance with the inputs for positioning received from the user; and
in response to a trigger signal of the user for moving the movable elements, driving the movable elements to cause the movable elements to adopt the displayed position.

The medical-technological apparatus, or medical apparatus for short, may, by way of example, be an X-ray apparatus or the like comprising movable elements that are adjustable by electric motors, hydraulic drives or other drives. In a preferred embodiment, the invention deals with a C-arm apparatus.

The representation of the model of the medical technological apparatus makes it possible, before the actual movement of the movable elements, to define the positions of the individual movable parts. The model thus indicates the end position of the individual movable elements that is set by a user. It is only if the user inputs the trigger signal that the actual movement is begun. In this case, the trigger signal can preferably be input via an input device, for example, which is safe in the sense of the first fault case. If the input device is designed as a touchscreen, for example, the touchscreen can comprise two different sensitive layers, e.g. a capacitive layer and a resistive layer for detecting inputs. It is only if both sensitive layers detect an input that the latter is also actually accepted as made. If the touchscreen comprises only one sensitive layer, e.g. a further switch, e.g. a foot-operated switch or the like, can be provided, which has to be actuated in addition to the touchscreen in order to identify the trigger signal as valid.

The invention enables an intuitive operation of the medical technological apparatus, in which the user can unambiguously identify the position into which the movable elements are moved, even before the latter begin a movement. In contrast to conventional operating units of medical technological apparatuses, such as e.g. simple joysticks customary heretofore, in which a movement of the medical technological apparatus or of the respective movable element is triggered immediately upon the actuation of the joystick, the probability of erroneous operation is thus significantly reduced.

Further, particularly advantageous configurations and developments of the invention are evident from the dependent claims and the following description, wherein the independent claims of one claim category can also be developed analogously to the dependent claims of another claim category and the features of different exemplary embodiments can be combined to form new exemplary embodiments.

In order to be able also to display the actual positions of the movable elements in addition to the target positions on the display device, in one embodiment the medical technological apparatus can comprise a number, that is to say one or a plurality, of sensors which are coupled to the movable elements and designed to detect the positions of the movable elements. The computing device can furthermore be coupled to the sensors and designed to represent simultaneously in the model the detected positions of the movable elements and the positions of the movable elements predefined by the inputs for positioning. The computing device can in this case identify e.g. in color for differentiation the movable elements in the detected positions and in the target positions predefined by the user. Alternatively or additionally, the computing device can represent the movable elements in the detected positions e.g. as solid or nontransparent bodies and can represent said movable elements in the positions predefined by the user e.g. as semitransparent superimpositions. During the movement of the movable elements, the representation of the movable elements on the display device can be tracked in accordance with the actual positions of the movable elements.

In order to enable the user to have a better view of the medical technological apparatus, the computing device can be designed to adapt the perspective in which the model is represented on the display device in accordance with perspective inputs. For this purpose, the input device can preferably be designed to receive perspective inputs from the user, which are then transferred to the computing device. In this case, "perspective inputs" should be understood to mean items of information, in particular control commands, which define this perspective of the display. The perspective inputs may be e.g. operating gestures on a touchscreen which are effected simultaneously with two fingers. A rotation of two opposite fingers on a circular path can lead e.g. to a corresponding rotation of the model. Alternatively, a perspective selection mode can also be selected and a movement of an individual finger on the touchscreen can be used to correspondingly rotate or scale the model of the medical technological apparatus. Predefined perspectives for selection can also be displayed to the user on the display device.

For simpler handling of the display device and the input device, the display device and the input device can be designed as a touch-sensitive screen. Such a touch-sensitive screen furthermore has the advantage that it manages without projecting discrete operating elements, such as e.g. buttons or joysticks, and is therefore easy to clean and/or sterilize.

In order to enable the medical technological apparatus to be viewed from different viewing angles, the display device and/or the input device, preferably in the form of the touch-sensitive screen, can be arranged releasably on a housing of the medical technological apparatus and can be coupled to further components of the medical technological apparatus via a, preferably wireless, communication connection. The medical technological apparatus can furthermore comprise a locating device designed to locate the display device and/or the input device or the touch-sensitive screen, wherein the computing device can be designed to adapt the representation of the model on the display device or the touch-sensitive screen to the relative position of the touch-sensitive screen with respect to the housing of the medical technological apparatus. The screen can be designed e.g. as a dedicated touchscreen provided as a component of the medical technological apparatus. Alternatively, however, the screen can e.g. also be a tablet PC on which a corresponding application for controlling the medical technological apparatus is implemented. A user can thus carry the display device and/or the input device or the screen with himself/herself while he/she moves around the medical technological apparatus. At the same time, on the basis of the locating of the display device and/or the input device or the screen, e.g. by means of a 3D camera or a radio-based locating system, corresponding perspective inputs for the computing device can be generated in order always to adapt the representation of the medical technological apparatus on the display device or the screen to the current position of the user. The user thus sees on the screen the model of the medical technological apparatus always in that perspective in which he/she sees the real medical technological apparatus in front of himself/herself. Movements of the movable elements on the model can thus be displayed in the perspective of the user and the probability of erroneous controls can be reduced.

In one embodiment, the computing device can be designed to identify in the representation of the model on the screen those features of the medical technological apparatus which serve for the movement of the movable elements on the real medical technological apparatus. Furthermore, the input device can be designed to accept inputs for positioning one of the movable elements only at the corresponding identified locations in the model. By way of example, on the display device handles of the medical technological apparatus can be highlighted which, on the real medical technological apparatus, serve for setting or moving the medical technological apparatus. In the case of a C-arm, e.g. handles can be provided for carrying out an orbital rotation. If a user then touches the corresponding handles on the screen, said user can likewise carry out an orbital rotation in the model. By means of rear handles identified in the model, the user can e.g. also change the position of the C-arm on the floor.

For exact positioning, in one embodiment the computing device can be designed to engage the movable elements at predefined engagement positions of an engagement lattice in the representation of the model on the display device. The computing device can provide e.g. a uniform engagement lattice having engagement points spaced apart uniformly from one another. The exact positioning of the individual movable elements is considerably simplified by means of such an engagement lattice. It may furthermore be provided, for example, that a user can set the resolution of the grid, that is to say the distance between the engagement points. Furthermore, engagement into one of the engagement points can be indicated to the user e.g. by an acoustic or tactile signal. In one embodiment, the engagement lattice can also be activated and deactivated by the user.

In one embodiment, the computing device may be configured to adapt the grid on the basis of a current position of the respective movable element on the real medical technological apparatus and/or to adapt the grid on the basis of a list of clinically relevant positions of the respective movable element. In the case of a C-arm or X-ray apparatus, the grid can have, on the basis of a current position of an axis, for example, an engagement point at an angle rotated by 90° in order to be able to provide lateral viewpoints of the current view in a simple manner. Additionally or alternatively, e.g. a list of clinically relevant positions of the movable elements, which can be used as further engagement points, can also be provided in the computing device. By way of example, the computing device can have a list of possible operations. If a user selects one of the operations, the computing device can use the corresponding clinically relevant positions of the respective operation as engagement points (e.g. Inlet/Outlet View in the case of pelvis operations). Furthermore, a user can also store a list of preferred positions which can be used as engagement points of the engagement lattice. Furthermore, during the operation it is possible to add the engagement points which are defined by the operator or which are oriented for example to directions of screws and implants which were detected in the X-ray images.

For simple repetition of positions already used, the computing device can be designed to store predefined positions for the movable elements and to display them to a user by means of the display device. The user can then select a respective one of the predefined positions via the input device. The predefined positions can in this case relate to all the movable elements. In order to move to one of the predefined positions, a user thus does not have to individually adapt each of the movable elements, but rather can set all the movable elements simultaneously by selecting one of the predefined positions. By way of example, the predefined positions can also comprise cleaning, transport or maintenance positions besides clinically relevant positions.

In one embodiment, the elements involved in the movement can be highlighted on the model during a movement. In particular, the direction of movement can be indicated in the model.

In one embodiment, it is possible to fit movement indicators at the movable elements, which, in the case of a movement of the movable elements are driven in each case by the computing device in order to indicate a movement of the movable parts. The movement indicators can be e.g. acoustic or optical signal sources. By way of example, an orbital rotation of a C-arm can be indicated by a cyclic signal tone. The cycle time can be dependent e.g. on the speed of the rotation. Furthermore, a movement can be indicated e.g. by corresponding lights, LEDs, light strips or LED strips on which a light signal moves in the corresponding direction of movement. In this case, the speed of the light signal can be dependent e.g. on the speed of movement of the respective movable element. In parallel with the identification of the movement at the movable elements, the respectively moving element can also be identified in the representation of the model.

In one embodiment, provision may be made of collision sensors for the movable elements, which are designed to monitor the movement space of the movable elements and to detect objects in the movement space of the movable elements, wherein the computing device can be designed, in the representation of the model, to identify a possible collision of a movable element with a detected object and to output a corresponding warning signal. By way of example, ultrasonic sensors which monitor the movement space of the individual movable elements can serve as collision sensors. As a result, as early as before or during a movement it is possible to ascertain whether the movement can be ended successfully. By way of example, even as early as before a movement is carried out, it is possible to indicate on the display device that the movement would cause a collision. The user can thus select an alternative movement before the movement actually begins. If the user implements the movement despite an indicated collision, the computing device can interrupt the movement before the collision takes place.

In order to be able also to take account of the surroundings of the medical technological apparatus in the representation, provision may be made of a camera system, designed to record a three-dimensional image of the surroundings of the medical technological apparatus, wherein the computing device can be designed to represent the environment detected by the camera system jointly with the model of the medical technological apparatus in the display device. By way of example, such a 3D camera system can detect an operating table or further operation systems which can be included in the representation on the display device. As a result, a realistic image of the situation in the medical technological apparatus can be shown to the user. In particular, the camera system can also serve as a collision sensor.

If the computing device identifies a possible collision of one of the movable elements with an object in the surroundings of the medical technological apparatus, the computing device can indicate to the user e.g. alternative movement sequences with which the respective position can be adopted without a collision occurring.

Other features which are considered as characteristic for the invention are set forth in the appended claims.

Although the invention is illustrated and described herein as embodied in controlling a medical technological apparatus, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
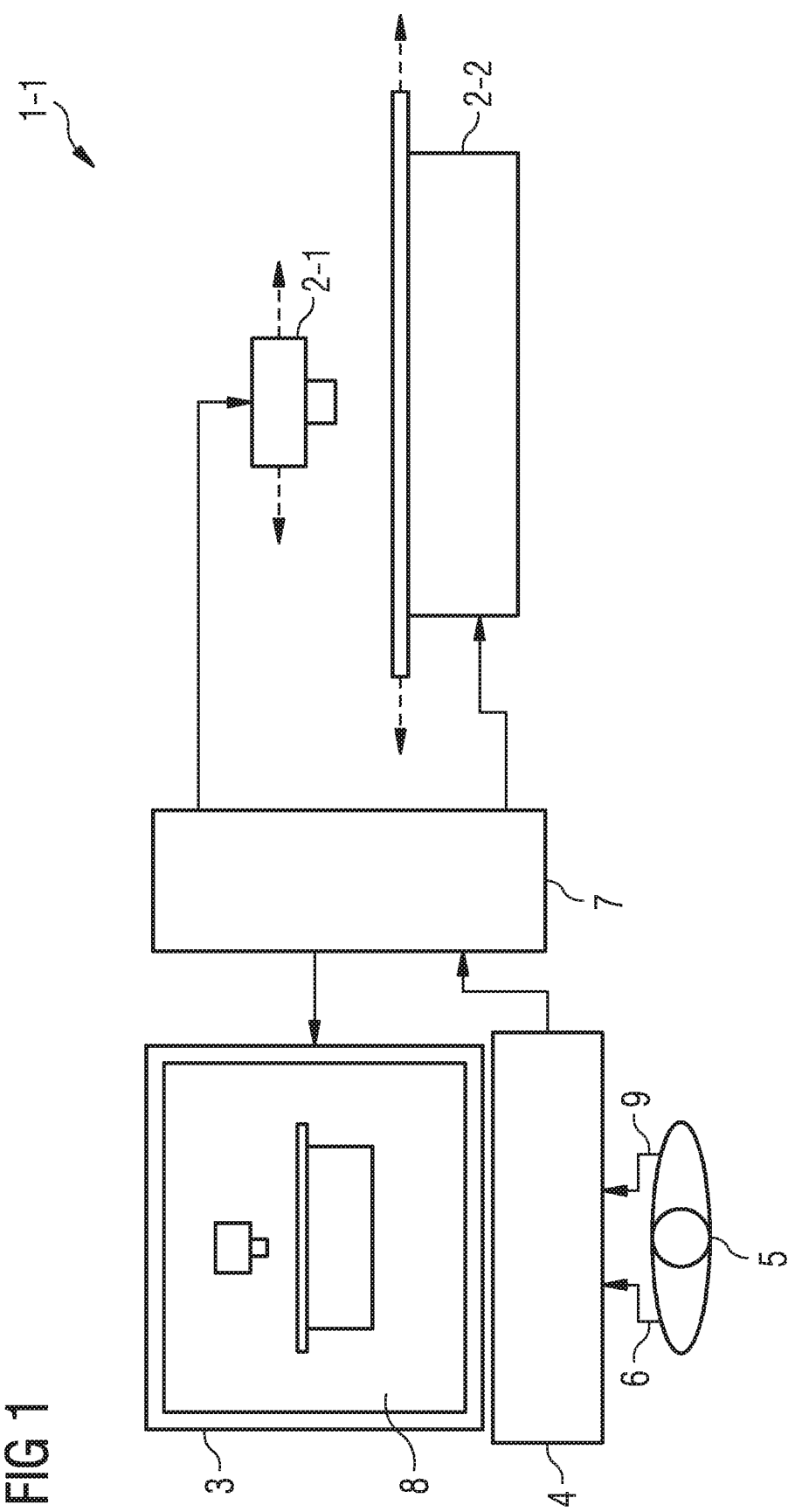
FIG. 1 shows a block diagram of an exemplary embodiment of a medical technological apparatus according to the invention.

Referring now to the figures of the drawing in detail and first, particularly, to FIG. 1 thereof, there is shown a medical technological apparatus 1-1, comprising two movable elements, an X-ray source 2-1 and a patient table 2-2. The selection and number of the movable elements 2-1, 2-2 is merely by way of example and it goes without saying that further or other movable elements are possible. At each of the movable elements 2-1, 2-2, two arrows toward the right and left indicate that said movable elements are movable.

The electrical drive units used for the movement of the movable elements 2-1, 2-2 are not illustrated separately.

The X-ray source 2-1 and the patient table 2-2 are coupled to a computing device or processor 7, which controls the movement of the X-ray source 2-1 and of the patient table 2-2. In order to enable a user 5 to control the movable elements 2-1, 2-2, the medical technological apparatus 1-1 includes an input device 4. Furthermore, a model 8 of the medical technological apparatus 1-1 or of the movable elements 2-1, 2-2 is displayed to the user 5 on a display device 3. The model 8 can be in particular a three-dimensional representation of the medical technological apparatus 1-1.

If the user 5 inputs, via the input device 4, inputs 6 for positioning the movable elements 2-1, 2-2, the latter are not moved directly. Rather, the representation of the model 8 in the display device 3 is adapted in accordance with the inputs 6. The computing device 7 thus represents the movable elements 2-1, 2-2 of the model 8 in those positions into which they would be moved as a result of the inputs 6 of the user 5.

The representation of the movable elements 2-1, 2-2 in the model 8 by the computing device 7 can be effected in various ways. As explained above, the computing device 7 can represent in the model 8 only the movable elements 2-1, 2-2 in accordance with the inputs 6 by the user 5. Alternatively, the computing device 7 can display in the model 8 the positions of the movable elements 2-1, 2-2 predefined by the inputs 6 as partly transparent superimpositions or the like above the medical technological apparatus 1-1 represented in the actual position.

In both cases, the user 5 can check the end positions of the movable elements 2-1, 2-2 on the model 8 before the user initiates the actual movement of the movable elements 2-1, 2-2 by means of a trigger signal 9. Such a trigger signal 9 may, for instance, be the actuation of a corresponding switch or pushbutton on the input device 4 or the actuation of a foot-operated switch. The separate implementation of the display device 3 and of the input device 4 is merely by way of example. In a further embodiment, the display device 3 and the input device 4 can be combined, for example, on a touchscreen or the like.

Figure 2:
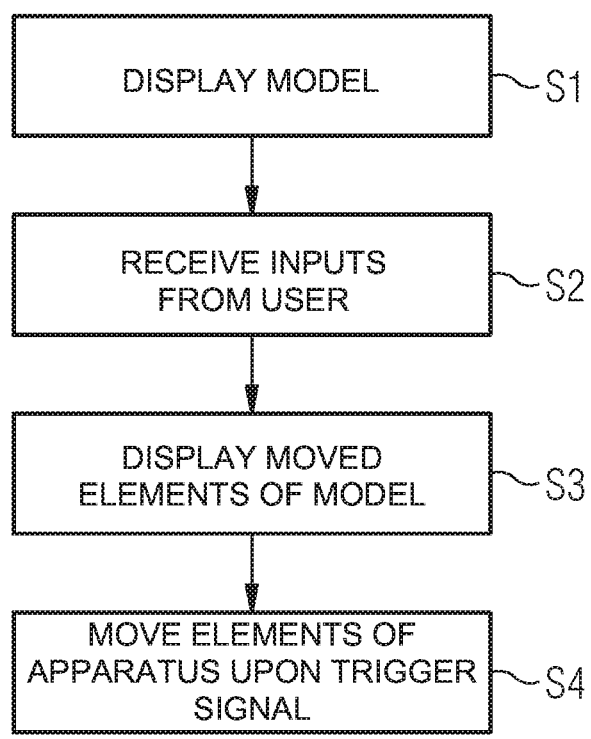
FIG. 2 shows a flow diagram of an exemplary embodiment of a method according to the invention.

The control method in FIG. 2 for a medical technological apparatus 1-1 to 1-3 comprising movable elements 2-1 to 2-5 displays a model 8 of the medical technological apparatus 1-1 to 1-3 to a user on a display device 3 in a first step S1. In order to control a movement of the movable elements 2-1 to 2-5, step S2 involves receiving inputs 6 for positioning the movable elements 2-1 to 2-5 from a user 5. However, the inputs 6, i.e., the input commands, are not converted directly into corresponding movements. Rather, in step S3, the movable elements 2-1 to 2-5 are represented in the model 8 in accordance with the received inputs 6. The user 5 thus sees the target positions of the movable elements 2-1 to 2-5 on the display device 3 before the actual movement of said movable elements. Finally, in step S4, the movable elements 2-1 to 2-5 are driven in response to a trigger signal 9 of the user 5 in such a way that they adopt the displayed position.

In order to be able to better adapt the representation of the model 8 on the display device to reality, the respective position can be detected for each of the movable elements 2-1 to 2-5. The display of the model 8 can be adapted in accordance with the detected position and comprise e.g. the actual positions of the movable elements 2-1 to 2-5 together with the target positions of the movable elements 2-1 to 2-5.

Furthermore, the user 5 can select the perspective in which the model 8 is represented on the display device 3. This enables the user 5 to view the model 8 from different directions and to check the target positions of the movable elements 2-1 to 2-5. However, the perspective can also be adapted automatically on the display device 3. Particularly in the case of a combined display and input device, such as e.g. a tablet PC, the user 5 or the tablet PC can be located, for example, and the representation of the model 8 on the display device 3 can be adapted to the relative position of the user 5 with respect to the medical technological apparatus 1-1 to 1-3. A camera system 16 can also be used for locating or detecting objects around the medical technological apparatus 1-1 to 1-3. Detected objects can then e.g. likewise be represented on the display device 3. This enables the user 5 to recognize possible collisions before a movement of the movable elements 2-1 to 2-5 begins.

Figure 3:
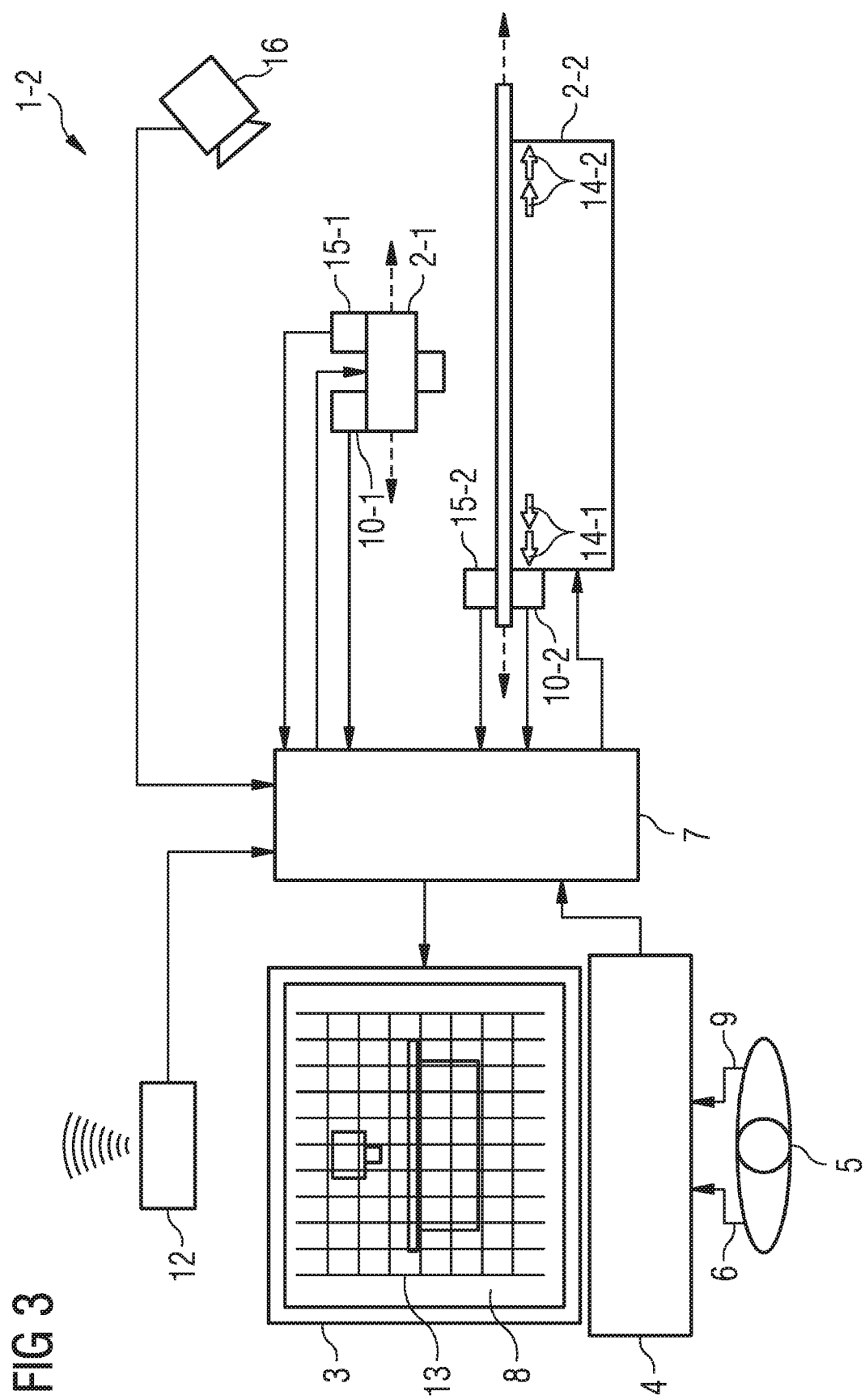
FIG. 3 is a block diagram of a further exemplary embodiment of a medical technological apparatus according to the invention.

FIG. 3 shows a further embodiment of a medical technological apparatus 1-2. The medical technological apparatus 1-2 is based on the medical technological apparatus 1-1 in FIG. 1 and differs therefrom to the effect that sensors 10-1, 10-2 for position detection and collision sensors 15-1, 15-2 are provided on the movable elements 2-1, 2-2. The position sensors 10-1 and 10-2 serve to detect respectively the current positions of the movable elements 2-1 and 2-2 and to communicate them to the computing device 7. The computing device 7, with the aid of this information, can represent the movable elements 2-1 and 2-2 in the model 8 in accordance with their current positions. The target positions of the movable elements 2-1, 2-2, which are predefined by the user 5 by the latter's inputs 6, can be represented by the computing device 7, e.g. as semitransparent superimpositions or the like in the model 8. The collision sensors 15-1, 15-2 serve to monitor the movement region of the respective movable element 2-1, 2-2 and to report possible collisions to the computing device 7. The latter can thereupon correspondingly adapt the representation of the model 8 and output a warning signal. By way of example, the computing device 7 can represent the semitransparent movable elements 2-1, 2-2 in the respective target positions as red or flashing red. It goes without saying that the collision sensors 15-1, 15-2 can also be coupled to a safety device (not illustrated separately) which stops a movement of the movable elements 2-1, 2-2, even without the assistance of the computing device 7, before a collision occurs.

A grid or an engagement lattice 13 is superimposed on the representation of the model 8 in FIG. 3. In this case, the engagement lattice 13 is illustrated merely by way of example as an equidistant lattice 13. Furthermore, the engagement lattice 13 can also be invisible, that is to say not represented in the display device 3. The points of the engagement lattice 13 may then be apparent merely by virtue of the fact that the movable elements 2-1, 2-2 engage into them in the course of a movement. Such engagement can be clearly highlighted for the user e.g. by a sound or a vibration of the input device 4.

The medical technological apparatus 1-2 furthermore comprises a locating device 12, which locates the user 5 or the display device 3 and provides the locating information to the computing device 7. The locating of the display device 3 enables the computing device 7, particularly in the case of a portable display device 3, e.g. a tablet PC or touchpanel, to adapt the perspective of the represented model 8 to the position of the display device 3. The computing device 7 can in particular also be designed to detect the inclination, that is to say the orientation, of the display device 3. This can be effected e.g. by the locating device 12. Alternatively, the display device 3 can e.g. have inclination sensors and communicate the information about its inclination to the computing device 7 e.g. wirelessly.

In FIG. 3 a camera system 16 is furthermore provided, which records in particular a three-dimensional image of the surroundings of the medical technological apparatus 1-2. A three-dimensional image can be recorded by the camera system 16 e.g. with the aid of two cameras, the images of which are evaluated by the computing device 7. However, the camera system 16 can also comprise one camera, which can capture depth information. It goes without saying that the camera system 16 can comprise a plurality of cameras and record the surroundings of the medical technological apparatus 1-2 from different perspectives. With the aid of the camera system 16, the computing device 7 can create a three-dimensional model of the surroundings of the medical technological apparatus 1-2. It is thus possible for the computing device 7 to identify objects in the surroundings of the medical technological apparatus 1-2. The computing device 7 can use the information about said objects, e.g. a patient lying on an operating table, to supplement the representation of the model 8 in the display device 3 by said objects. Consequently, not just the model 8 of the medical technological apparatus 1-2 is displayed to the user. Rather, the entire surroundings of the medical technological apparatus 1-2 are likewise displayed to the user 8.

In particular, the computing device 7 can also use the information about the objects to calculate whether a movable element 2-1, 2-2 can move to a target position without colliding with one of the objects. Should one of the movable elements 2-1, 2-2 collide with an object on the way to a target position, the computing device 7 can also calculate alternative movement sequences and propose them to the user 5.

Finally, merely by way of example, movement indicators 14-1, 14-2 in the form of arrows, the illumination of which is controllable by the computing device 7, are fitted to the movable element 2-2 of the medical technological apparatus 1-2. By way of example, the computing device 7 can cause the left arrows 14-1 to flash in the case of a movement of the movable element 2-2 toward the left.

In FIG. 3 the display device 3 and the input device 4 are illustrated as separate units. In one embodiment, they can also be designed jointly as a touch-sensitive screen 11, e.g. a tablet or a tablet PC. In such an embodiment, the user 5 can effect his/her inputs 6 directly on the touch-sensitive screen 11. Movements of the individual movable elements 2-1, 2-2 into the target positions can be defined by the user 5, e.g. by touching and dragging the respective movable element 2-1, 2-2 on the touch-sensitive screen 11.

Figure 4:
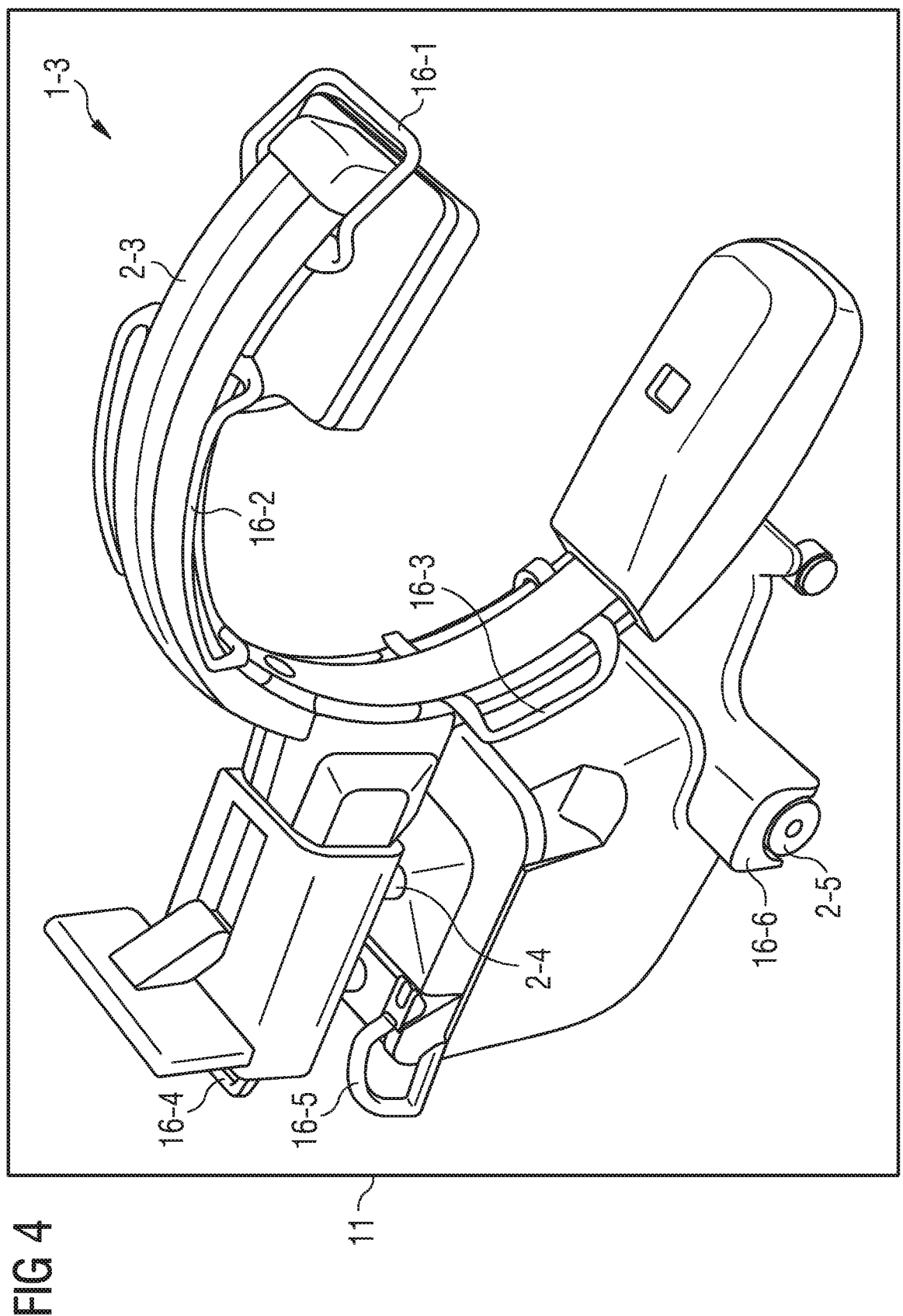
FIG. 4 shows a representation of a model of a medical technological apparatus on a display device according to the invention.
Figure 5:
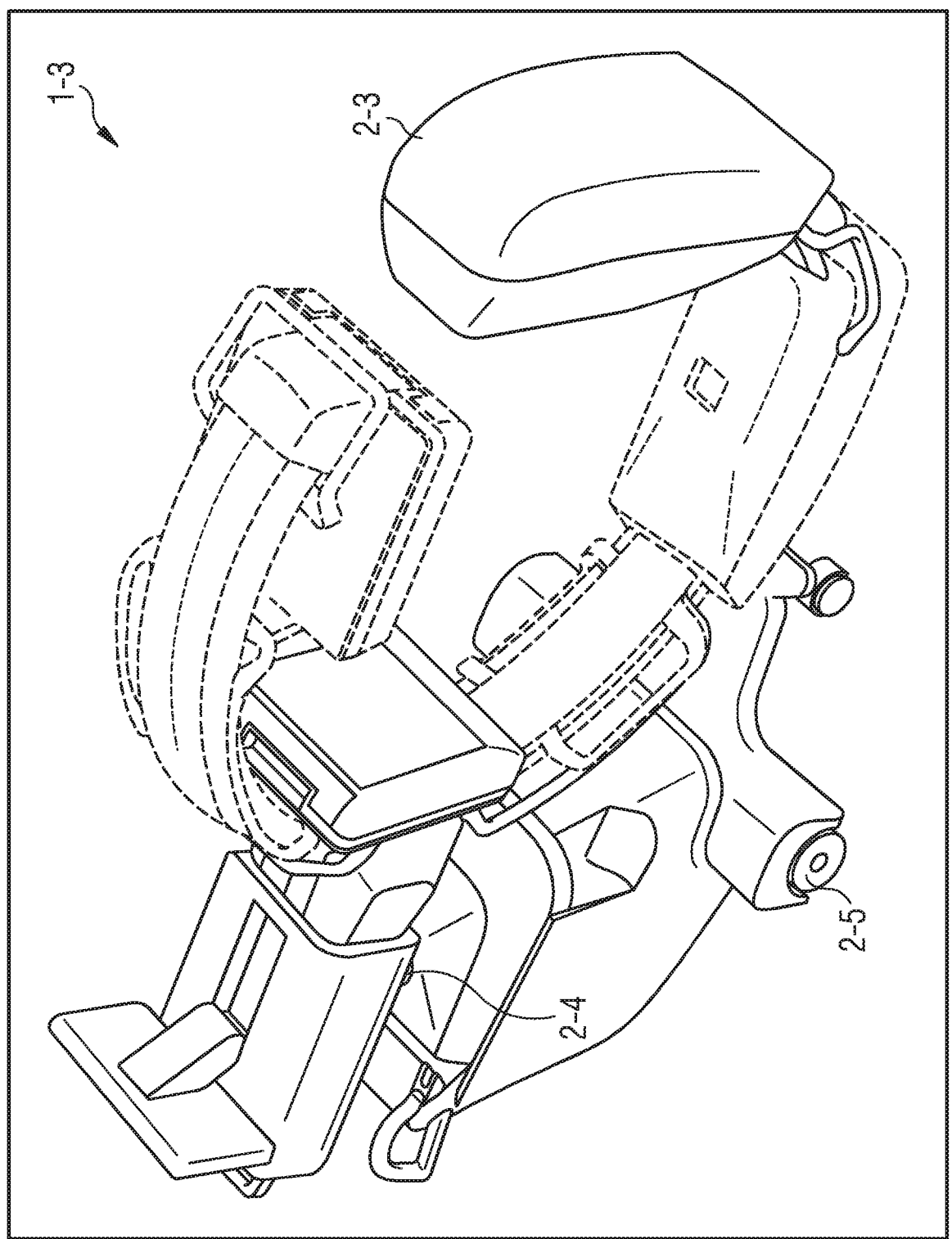
FIG. 5 shows a further representation of a model of a medical technological apparatus on a display device according to the invention.

FIG. 4 and FIG. 5 show possible representations of a C-arm apparatus or C-arm 1-3 on a touch-sensitive screen 11.

The C-arm 1-3 has an arc 2-3, a vertical spindle 2-4 and wheels 2-5 as movable elements. FIG. 4 illustrates the C-arm 1-3 in its current position. The user 5 has not yet effected any inputs 6 at all. The representation of the C-arm 1-3 on the touch-sensitive screen 11 thus corresponds to the actual position of the C-arm 1-3.

In order to enable an intuitive handling of the C-arm with the touch-sensitive screen 11, the computing device 7 can accept inputs 6 of the user 7 e.g. only at those locations at which the real C-arm can be gripped and moved by the user. In FIG. 4 e.g. handles 16-1 to 16-5 and wheels 16-6 are marked, which serve for the movement of the individual elements 2-3 to 2-5 on the real C-arm 1-3. The handles 16-1, 16-2 and 16-3 serve for moving the arc 2-3. The handle 16-4 serves for vertically moving the vertical spindle 2-4 of the C-arm 1-3. Finally, the handle 16-5 and the wheels 16-6 serve for displacing the C-arm 1-3 on the floor.

The computing device 7 may then permit and represent only a movement of the arc 2-3 e.g. in the event of the handles 16-1 to 16-3 being touched on the touch-sensitive screen 11. In the event of the handle 16-4 being touched, the computing device 7 may thus merely enable an adjustment of the vertical spindle 2-4 of the C-arm 1-3. Finally, a displacement of the C-arm 1-3 on the floor is possible in the event of the handle 16-5 or the wheels 16-6 being touched.

In FIG. 5 the arc 2-3 of the C-arm 1-3 is situated in a position in which the opening thereof points upward. The user 5 has already defined a target position for the arc 2-3 with an input 6 (FIG. 3), in which target position the arc is rotated from its current position by 90° in the clockwise direction. The target position is represented by dashed lines in FIG. 5. In the representation on the touch-sensitive screen 11, the arc 2-3 may be represented e.g. as semitransparent. This superimposition can be placed over the C-arm 1-3 represented as a solid body in its current position. The user can thus see the current position and the target position of the arc 2-3 simultaneously and coordinate them with one another.

If the computing device, as described above, ascertains that one of the movable elements 2-3 to 2-5 in its target position would collide with an object, it can represent the respective movable object in the target position e.g. as red or flashing. If a movement into the target position is possible without a collision, the computing device 7 can represent the respective movable element 2-3 to 2-5 e.g. as green.

Finally, it is pointed out once again that the medical technological apparatuses and methods described in detail above are merely exemplary embodiments which can be modified in diverse ways by the person skilled in the art, without departing from the scope of the invention. Furthermore, the use of the indefinite article "a" or "an" does not exclude the fact that the relevant features can also be present in a plurality. Likewise not excluded is the situation where elements of the present invention that are illustrated as individual units consist of a plurality of interacting subcomponents, which if appropriate can also be spatially distributed.

The following is a summary list of reference numerals and the corresponding structure used in the above description of the invention:

1-1 to 1-3 Medical apparatus
2-1 to 2-5 Movable elements
3 Display device
4 Input device
5 User
6 Inputs
7 Computing device
8 Model
9 Trigger signal
10-1, 10-2 Sensors
11 Touch-sensitive screen
12 Locating device
13 Engagement lattice
14-1, 14-2 Movement indicators
15-1, 15-2 Collision sensors
16 Camera system
S1-S4 Method steps

The invention claimed is:
1. A medical imaging apparatus, comprising:
a plurality of movable elements;

a display device and an input device being a touch-sensitive screen configured to receive inputs for positioning said movable elements from a user;

a computing device connected to said display device and configured to receive input commands for positioning said movable elements via said input device, said computing device being configured to display a model of the medical apparatus on said display device, to display said movable elements in the model in accordance with the input commands received from said input device at target positions that are different from actual positions of the movable elements of the medical apparatus and, in response to a trigger signal input by a user, to drive said movable elements of the medical apparatus to adopt a target position as displayed on said display device, wherein an actual movement of said movable elements of the medical apparatus is only begun when the user inputs the trigger signal;

a locating device configured to locate a user or the display device and to provide locating information to said computing device;

said computing device being configured to adapt a perspective of the display on said display device to a position of said display device on a basis of the locating information received from said locating device; and said computing device being configured to identify in a representation of the model on the touch-sensitive screen those features of the medical apparatus which serve for moving said movable elements and said input device being configured to accept inputs for positioning one of said movable elements only at a correspondingly identified location in the model.

2. The medical apparatus according to claim 1, comprising a plurality of sensors connected to said computing device and coupled to said movable elements for detecting positions of said movable elements, wherein said computing device is configured to represent simultaneously in the model the detected positions of the movable elements and the positions of the movable elements predefined by the input commands for positioning.

3. The medical apparatus according to claim 1, wherein said computing device is configured to adapt a perspective view in which the model is represented on said display device on a basis of perspective inputs, and wherein said input device is configured to receive perspective inputs from the user.

4. The medical apparatus according to claim 1,
which further comprises a housing; and
wherein one or both of said display device and said input device are releasably mounted to said housing and are coupled to further components of the medical apparatus via a communication connection; and
further comprising a locating device configured to locate said display device and/or the input device; and
wherein said computing device is configured to adapt the representation of the model on the display device to a relative position of said display device and/or of said input device with respect to said housing of the medical apparatus.

5. The medical apparatus according to claim 1, wherein said computing device is configured to snap said movable elements at predefined engagement positions of an engagement lattice in the representation of the model on said display device on occasion of a movement of the movable elements by the user.

6. The medical apparatus according to claim 5, wherein said computing device is configured:

to adapt the engagement lattice on a basis of a current position of a respective said movable element on the medical apparatus; and/or to adapt the engagement lattice on a basis of a list of clinically relevant positions of the respective said movable element.

7. The medical apparatus according to claim 1, wherein said computing device is configured to store predefined positions for said movable elements, to display the predefined positions to a user via said display device, and to enable the user to select a respective one of the predefined positions via said input device.

8. The medical apparatus according to claim 1, further comprising movement indicators at said movable elements which, in a case of a movement of said movable elements are driven in each case by said computing device in order to indicate a movement of said movable elements.

9. The medical apparatus according to claim 1, further comprising collision sensors for said movable elements, said collision sensors being configured to monitor a movement space of said movable elements and to detect objects in the movement space of said movable elements, wherein said computing device is configured, in the representation of the model, to identify a potential collision of a respective said movable element with a detected object and to output a corresponding warning signal.

10. The medical apparatus according to claim 1, further comprising a camera system configured to record a three-dimensional image of the surroundings of the medical apparatus, wherein said computing device is configured to represent an environment detected by said camera system jointly with the model of the medical apparatus in said display device.

11. A method of controlling a medical imaging apparatus having movable elements selected from the group consisting of a patient table, an X-ray source and a C-arm of an X-ray machine, the method comprising:

displaying a model of the medical imaging apparatus on a touch-sensitive screen, and thereby identifying those features of the medical imaging apparatus in the representation of the model on the touch-sensitive screen which serve for moving the movable elements on the medical imaging apparatus;

receiving inputs for positioning the movable elements entered by a user via the touch-sensitive screen, and thereby only accepting inputs for positioning one of the movable elements only at a correspondingly identified location in the model;

displaying the movable elements in the model at target positions that are different from actual positions of the movable elements of the medical imaging apparatus in accordance with the inputs for positioning received from the user;

locating the user or the touch-sensitive screen relative to the medical imaging device, and adapting a perspective of a display on the screen to a position of the user or the screen; and in response to a trigger signal of the user for moving the movable elements of the medical imaging apparatus, driving the movable elements of the medical imaging apparatus to cause the movable elements to move from the actual positions of the movable elements and to adopt the displayed position, wherein an actual movement of the movable elements of the medical imaging apparatus is only begun when the user inputs the trigger signal.

12. The method according to claim 11, which comprises carrying out one or more of the following steps:
- detecting the positions of the movable elements, and simultaneously displaying in the model the detected positions of the movable elements and the positions of the movable elements predefined by the inputs for positioning; and/or
- receiving perspective inputs and adapting a perspective in which the model is represented on the display device in accordance with the perspective inputs; and/or
- indicating a movement of the movable elements by way of movement indicators on the movable elements; and/or
- locating a user of the medical apparatus and adapting a representation of the model on the display device to a relative position of the user with respect to a housing of the medical apparatus.

13. The method according to claim 11, which comprises:
- detecting objects in a movement space of the movable elements and identifying a potential collision of a respective movable element with a detected object in the representation of the model, and, if appropriate, outputting a corresponding warning signal; and/or
- recording a three-dimensional image of a surrounding space of the medical apparatus and representing a detected environment jointly with the model of the medical apparatus on the display device.

14. A medical imaging apparatus, comprising:
- a plurality of movable elements of one or more medical devices selected from the group consisting of a patient table, an X-ray source and a C-arm of an X-ray machine;
- a display device and an input device being a touch-sensitive screen configured to receive inputs for positioning said movable elements from a user;
- a computing device connected to said display device and configured to receive input commands for positioning said movable elements via said input device, said computing device being configured to display a model of the medical apparatus on said display device, to display said movable elements in the model in accordance with the input commands received from said input device at target positions that are different from actual positions of the movable elements of the medical apparatus and, in response to a trigger signal input by a user, to drive said movable elements of the medical apparatus to adopt a target position as displayed on said display device, wherein an actual movement of said movable elements of the medical apparatus is only begun when the user inputs the trigger signal; and
- said computing device being configured to identify in a representation of the model on the touch-sensitive screen those features of the medical apparatus which serve for moving said movable elements and said input device being configured to accept inputs for positioning one of said movable elements only at a correspondingly identified location in the model; and
- said computing device being configured to store predefined positions for said movable elements, to display the predefined positions to the user on said touch-sensitive screen, and to enable the user to select a respective one of the predefined positions via said input device.

* * * * *